United States Patent [19]

Fowler et al.

[11] Patent Number: 5,417,395
[45] Date of Patent: May 23, 1995

[54] MODULAR INTERCONNECTING COMPONENT SUPPORT PLATE

[75] Inventors: James Fowler, Hilliard; Charles Patzer, Columbus; Warren Nicholson; Wendell Thompson, both of Dublin, all of Ohio

[73] Assignee: Medex, Inc., Hilliard, Ohio

[21] Appl. No.: 85,352

[22] Filed: Jun. 30, 1993

[51] Int. Cl.⁶ .............................................. A47B 96/06
[52] U.S. Cl. ...................... 248/221.3; 128/DIG. 26; 604/151
[58] Field of Search ................. 248/221.3, 221.4, 125, 248/121; 361/732, 735; 604/151; 128/DIG. 26

[56] References Cited

U.S. PATENT DOCUMENTS

| | | |
|---|---|---|
| Re. 33,360 | 10/1990 | Reynolds et al. . |
| Re. 33,518 | 1/1991 | McCord et al. . |
| D. 283,441 | 4/1986 | Vcelva et al. . |
| 944,312 | 12/1909 | Brede . |
| 2,371,433 | 3/1945 | Davis . |
| 2,762,595 | 9/1956 | Jenne . |
| 3,081,023 | 3/1963 | Taylor . |
| 3,269,550 | 8/1966 | Marcus . |
| 3,429,450 | 2/1969 | Lambert . |
| 3,452,954 | 7/1969 | Lucietto et al. . |
| 3,526,040 | 9/1970 | Young . |
| 3,581,929 | 6/1971 | Guenard . |
| 3,592,187 | 7/1971 | Youdin et al. . |
| 3,599,828 | 8/1971 | Conway et al. . |
| 3,724,274 | 4/1973 | Millar . |
| 3,855,439 | 12/1974 | Hermann . |
| 4,034,612 | 7/1977 | Buckwitz . |
| 4,093,076 | 9/1977 | Halverson . |
| 4,099,626 | 7/1978 | Magnussen, Jr. . |
| 4,182,367 | 1/1980 | Day . |
| 4,227,420 | 10/1980 | Lamadrid . |
| 4,348,899 | 9/1982 | Muller . |
| 4,410,095 | 10/1983 | Dembicks . |
| 4,416,040 | 11/1983 | Towsley . |
| 4,422,794 | 12/1983 | Deken . |
| 4,491,015 | 1/1985 | Allemano . |
| 4,524,938 | 6/1985 | Strahs et al. . |
| 4,566,597 | 1/1986 | Caputo et al. . |
| 4,574,811 | 3/1986 | Stephens . |
| 4,597,291 | 7/1986 | Motomiya . |
| 4,611,822 | 9/1986 | Bernhardson . |
| 4,619,431 | 10/1986 | Matsui ......................... 248/221.4 X |
| 4,688,864 | 8/1987 | Sorel .............................. 361/735 X |
| 4,717,195 | 1/1988 | Okuyama et al. . |
| 4,770,297 | 9/1988 | Chang . |
| 4,772,217 | 9/1988 | Petersen . |
| 4,776,343 | 10/1988 | Hubbard et al. . |
| 4,838,865 | 6/1989 | Flank et al. . |
| 4,856,658 | 8/1989 | Novak . |
| 4,944,693 | 7/1990 | Puerner . |
| 4,970,900 | 11/1990 | Shepherd et al. . |
| 4,987,661 | 1/1991 | Kasai . |
| 5,016,312 | 5/1991 | Frimely . |
| 5,046,625 | 9/1991 | Rushing . |
| 5,112,019 | 5/1992 | Metezler ....................... 248/125 X |
| 5,155,663 | 10/1992 | Harase .......................... 361/740 X |
| 5,222,946 | 6/1993 | Kamen ............................... 604/151 |
| 5,275,367 | 1/1994 | Frye ................................ 248/205.3 |
| 5,322,253 | 6/1994 | Stevens ........................... 248/125 X |

FOREIGN PATENT DOCUMENTS

| | | |
|---|---|---|
| 0201207 | 11/1986 | European Pat. Off. . |
| 1049697 | 1/1952 | France . |
| 1467702 | 2/1966 | France . |
| 2287827 | 5/1976 | France . |
| 2619151 | 4/1976 | Germany . |
| WO92/07396 | 4/1992 | WIPO . |
| WO93/10835 | 6/1993 | WIPO . |
| WO93/19318 | 9/1993 | WIPO . |

Primary Examiner—J. Franklin Foss
Attorney, Agent, or Firm—Wood, Herron & Evans

[57] ABSTRACT

A modular interconnecting component support unit has a rigid plate (14) with a planar face (16) and a rib (24) and a slot (38) extending parallel the plate face but from opposite sides or edges (22, 34) of the plate so that two such units may be slid together while their faces are in planar relationship. Locking arms (46) adjacent the ends (40) of the slots (38) are provided to releasably grip a rib (24) of one unit received in the slot (38) of a second unit. A medical device, such as a reusable portion of a medical pressure transducer (20), may be permanently affixed to the plate face (16).

42 Claims, 4 Drawing Sheets

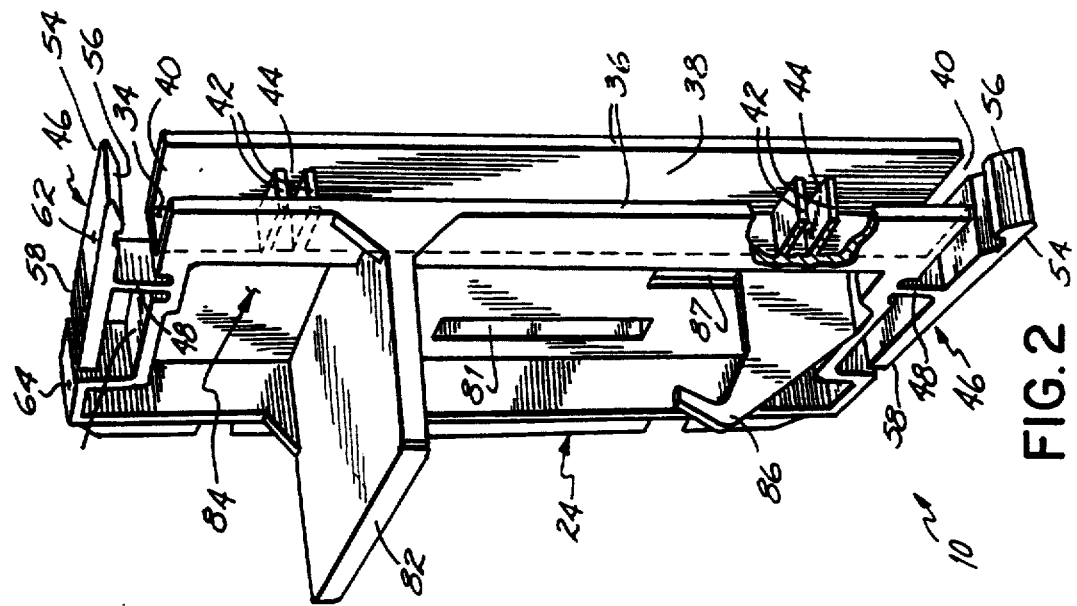
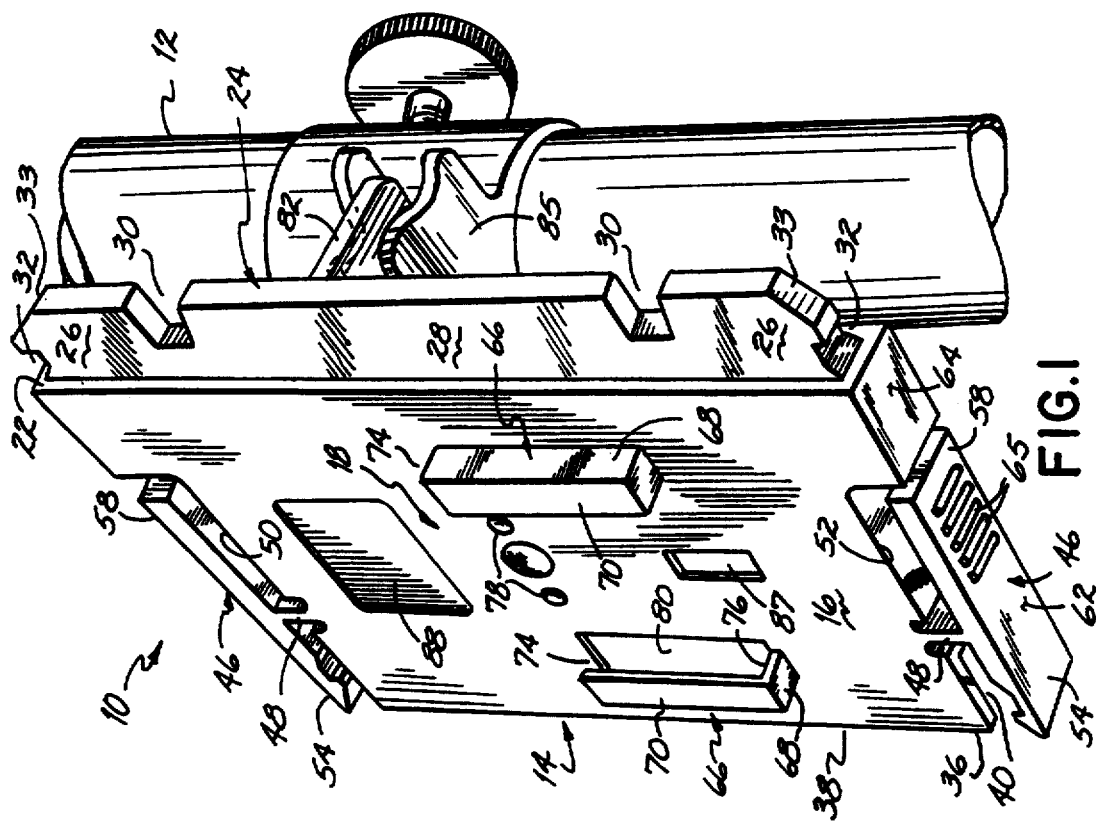
FIG. 1
FIG. 2

MODULAR INTERCONNECTING COMPONENT SUPPORT PLATE

BACKGROUND OF INVENTION

I. Field of the Invention

The present invention relates to modular interconnecting units for supporting devices, and, more specifically, to modular interconnecting plates used for supporting medical devices such as transducers, flush valves, stop cocks and the like.

II. Description of Prior Art

In hospital environments, for example, many procedures involve inserting one or more catheters into a patient with lengths of tubing extending therefrom. Connected to the tubing may be a variety of medical devices such as transducers, flush valves, stop cocks and the like. The tubing may become entangled, making it difficult for medical providers who need to use the devices to access them as needed. To organize the tubing and medical devices for quicker and safer access by medical personnel, and to additionally protect the devices from damage, it has been found to be beneficial to hold the devices to a mounting plate, which is in turn secured to an intravenous pole or other nearby structure. The mounting plates have a flat face with one or more receptacles formed thereon for holding the various medical devices at the ready.

While the use of mounting plates is advantageous, the number of medical devices to be supported may vary depending upon the needs of the patient. In some cases, a mounting plate having one receptacle may be all that is needed. In other cases, mounting plates capable of supporting two or more devices may be desired. Thus, the size of the plate needed may vary from patient to patient resulting in hospitals keeping several different sizes of mounting plates (i.e., with different numbers of receptacles) readily available.

One proposal to eliminate mounting plates of different sizes is a modular system of interlocking plates, each plate having its own receptacle for supporting a device, and structure to lock the plates to one another to simulate a larger plate having multiple receptacles. Such a system permits medical personnel to form any size plate necessary depending upon the medical needs of the patient. While such an interlocking system is desirable, a current modular system is considered to be clumsy in operation. For example, tubing may become tangled due to the offsetting of the plate faces as they are connected together. Similarly, the plates are difficult to separate and thus present not only inconvenience to medical providers but also could result in the tearing of a glove, for example, placing the user at risk of injury.

SUMMARY OF THE INVENTION

The present invention provides a modular interconnecting component support plate system which overcomes drawbacks associated with the current modular system. More specifically, the modular plates of the present invention may be easily and quickly connected together to form variable size plates and may just as easily and quickly be separated into the individual modules, all without unnecessarily tangling the tubing or exposing medical providers to injury or inconvenience. To this end, and in accordance with the principles of the present invention, each modular mounting plate is provided with a male web such as a rib running along one side edge of the plate and a female receptacle slot (for receiving the rib from a similar unit) running along the opposite side edge, with the sidewalls defining the slot and the rib extending from the plate in opposite directions, but parallel to the face of the plate. As a result, the rib of one plate is slidably receivable into the slot of another plate while the faces are maintained in generally the same plane rather than offset from one another.

The rib and slot cooperate to connect the plates such that they simulate a conventional multiple receptacle plate. Formed within the slot may be one or more rib stops which cooperate with recesses formed in the rib to prevent the rib from sliding up and down within the slot. To hold the two plates together, locking arms are mounted adjacent each lateral end of the slot to grip the lateral ends of the rib received therein.

A plurality of such plates may be releasably interconnected together into a system capable of supporting any desired number of devices by merely sliding or clipping the rib of one plate into the slot of another until the rib ends engage the locking arms. To release the units, the locking arms are manipulated to release the rib and allow the plates to be slid apart. The locking arms are advantageously mounted in lever-like fashion between the side edges and along the top and bottom edges of the plate, with the distal gripping ends positioned over the ends of the slot. By pressing the proximal ends of the locking arms towards the plate the distal ends pivot away from the slot, thereby freeing the rib and allowing two connected plates to be simply and readily slid apart. By thus positioning the locking arms, the plates are easily connected together and taken apart without undue inconvenience or risk of injury to the users.

To further enhance use of the system of the present invention, a portion of the top and bottom edges of the plate may be recessed with the locking arms received in the recesses so that the outer sides of the locking arms are generally flush with the nonrecessed portion of the top and bottom plate edges. As a result, there is a reduced risk of exposure to edges that might otherwise snag the glove of a user, for example.

The modular system of the present invention may be adapted to provide other conveniences to the user as well. More specifically, and in accordance with a further aspect of the invention, a medical device may be built directly into or permanently affixed onto a modular plate thereby eliminating the need for the user to couple the device to the plate, thus reducing the possibility that the device would come away from the plate in use. By way of example, a disposable medical pressure transducer may be generally permanently affixed, such as with adhesive, to the plate face such that when use of the transducer is completed, the entire module is disposed. Alternatively, and with reference to typical two-part medical transducers having a disposable fluid dome with a reusable transducer housing, the two parts must be put together with the respective diaphragms thereof in confronting engagement, and the reusable housing mounted in turn to the mounting plate. To eliminate one of those steps, and to reduce the risk that the assembled dome/housing unit may separate from the mounting plate, the reusable portion may be built directly into the modular plate. To this end, an aperture is formed through the face of the plate and the reusable diaphragm held thereacross. The sensor of the transducer is affixed behind the diaphragm and placed in communication therewith to fully perform the function of the reusable transducer housing. The receptacle structure on the face of the plate is configured to receive a disposable fluid dome with its diaphragm in confronting engagement with the diaphragm held by the plate face.

By virtue of the foregoing, there is thus provided a system of modular interconnecting component support plates that may be easily, quickly and reliably connected to and disconnected from a number of similar such plates to form a mounting plate able to support a number of devices without the need and cost associated with storing mounting plates of differing sizes. Additionally, the resulting composite plate may be separated into its individual modular mounting plates as easily, quickly and reliably as it was assembled. Still further, by permanently including a medical device with a modular plate, the use is advantageously simplified. Thus, for example, by incorporating the reusable portion of a medical transducer directly into the modular mounting plate, the complexity and time required to secure the transducer assembly to the mounting plate is reduced as is the risk of damage to the transducer unit.

These and other objects and advantages of the present invention shall become apparent from the accompanying drawings and the detailed description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention, FIG. 1 is a front perspective view of a modular mounting plate in accordance with the principles of the present invention and shown attached to a pole;

FIG. 2 is a rear perspective view of the modular mounting plate of FIG. 1;

DETAILED DESCRIPTION OF THE DRAWINGS

Figure 5:
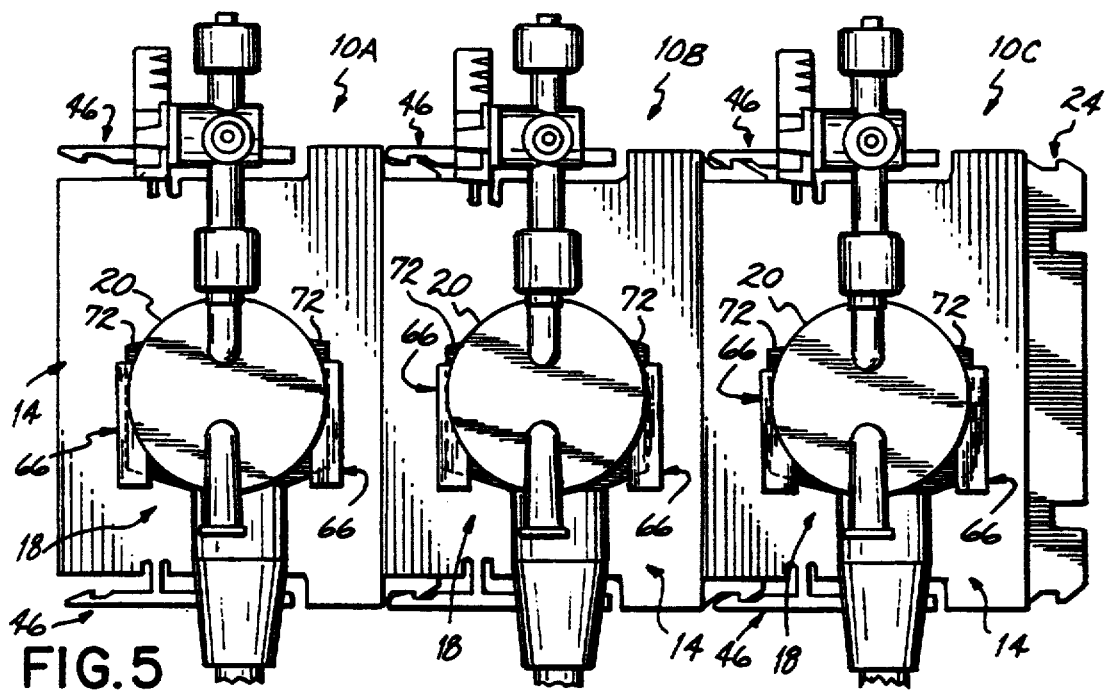
FIG. 5 is a schematic plan view of three modular plates of FIG. 1 interconnected into a single assembly.

With reference to FIGS. 1 and 2, there is shown a modular mounting plate 10 attached to an intravenous pole 12 (FIG. 1) for supporting devices as will be described. Mounting plate 10 comprises a rigid plate 14 having a generally planar front face 16 with a receptacle 18 thereon to support a device such as a transducer 20 (see FIG. 5). Extending along the length of right side edge 22 of plate 14 is a rib 24 having a width of about 0.15 inches that extends outwardly from edge 22 about 0.37 inches in a direction generally parallel to face 16. Rib 24 includes upper and lower segments 26, and middle segment 28 defined between recesses 30. The outer ends of upper and lower segments 26 have notches 32 behind cam faces 33 for a purpose to be described hereinafter. Extending along the length of the left side edge 34 of plate 14 are sidewalls 36 extending outwardly about 0.37 inches in a direction generally parallel to face 16 thereby defining a slot 38 having open ends 40. Sidewalls 36 are spaced apart about 0.15 inches to snugly receive therebetween a rib 24 from another mounting plate 10 to prevent the plates 10 from racking when they are interconnected. Protruding from the edge 34 (which also defines the floor of slot 38) are one or more rib stops 42 that fit into recesses 30 in rib 24 to prevent rib 24 from sliding longitudinally within slot 38 when two plates are interconnected. Rib stops 42 may merge with sidewalls 36 and be slotted as at 44 for ease of production.

Figure 3:
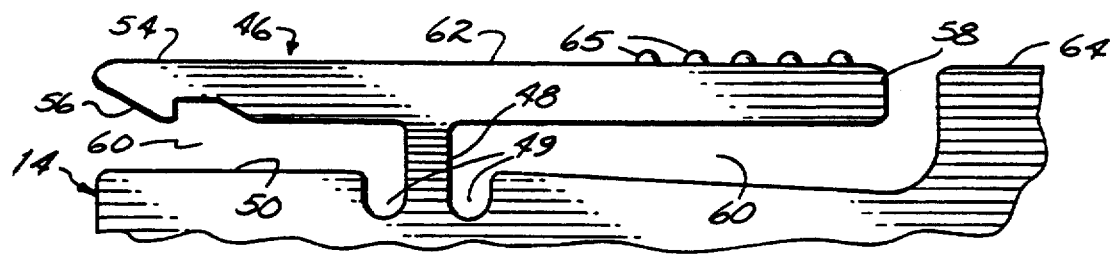
FIG. 3 is an enlarged front view of a locking arm of the mounting plate of FIG. 1.
Figure 4:
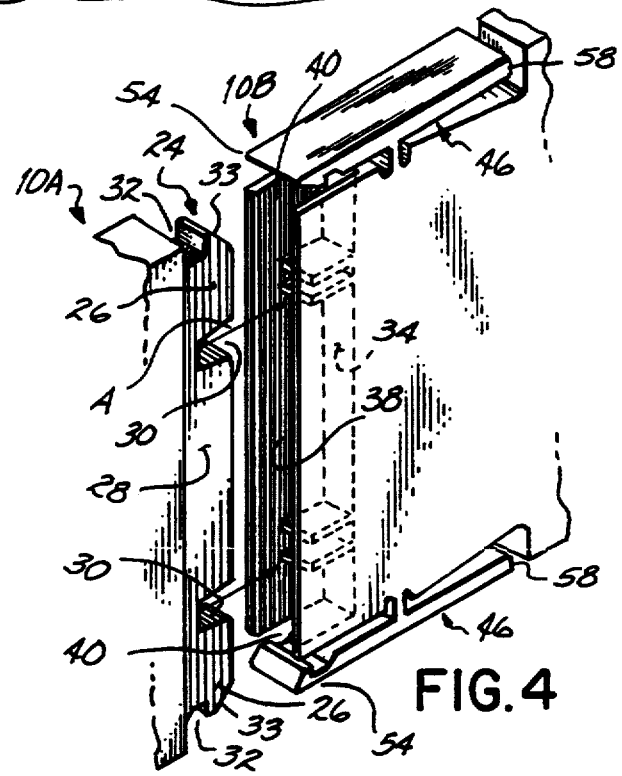
FIG. 4 is a diagrammatic view describing the ease of interconnecting and disconnecting the mounting plates of FIG. 1.

Locking arms 46 are provided to lock two plates 10 together. Arms 46 are pivotally connected by pivot member 48 in well 49 of intermediate top edge 50 and intermediate bottom edge 52 of plate 14 (see FIG. 3). The distal end 54 of each arm 46 extends over a respective open end 40 of slot 38 with detent 56 of distal end 54 facing into slot 38. As the rib 24 of one plate 10 slides laterally into slot 38 along a path identified by arrow A in FIG. 4, detents 56 ride over cam faces 33 on the ribs 24 and snap into notches 32 to securely lock the plates together (see FIG. 5). To unlock the plates, proximal end 58 of locking arms 46 are depressed to pivot the distal ends 54 outwardly from their respective edges 50 or 52 and slot 38, thereby disengaging detents 56 from notches 32, whereby one plate may be slid free of the other in a direction opposite arrow A (see FIG. 4).

Right edge 22 of plate 14 is longer than left edge 34. For example, edge 22 may be about 3.0 inches long whereas edge 34 is about 2.6 inches long. This size relationship provides some useful advantages. For example, upper and lower segments 26 of rib 24 extend beyond open ends 40 of slot 38 thereby permitting the locking arm detents 56 to engage the rib notches 32. Similarly, the areas 60 of top and bottom edges 50, 52, in which locking arms 46 are located, provide a recess such that outer surface 62 of each locking arm 46 is substantially co-extensive with the nonrecessed portion 64 of the respective top or bottom edge 50 or 52 of the plate. As a consequence, exposure to edges is reduced. Surfaces 62 may each include a plurality of rumple strips 65 formed thereon to facilitate finger gripping. Note also that the area 60 adjacent right edge 22 is angled downwardly to align with the proximal ends 58 of locking arms 46 when they are depressed.

As is conventional, support structure such as a receptacle 18 is formed in plate face 16 as seen in FIG. 1. Receptacle 18 comprises a pair of confronting channels 66 spaced about 1.02 inches apart and formed by L-shaped walls 68 extending forwardly from plate face 16, and an outer wall 70 connected to the distal edge of each wall 68. The wings of a device to be held by plate 10 (such as wings 72 of transducer 20 seen in FIG. 5) are slidably fit into channels 66 through open ends 74 until resting against the bottom ledge 76 of wall 68. A pair of raised dimples 78 protrude forwardly from plate face 16 between opposed channels 66 and bear against the mounted device to help hold it to mounting plate 10. Slots 80 and 81 may be provided through plate 14 beneath opposed channels 66. While a conventional receptacle 18 is shown, it will be appreciated that many other structures including, by way of example, opposed resilient clips or tabs, may be used to secure the devices to the mounting plate 10.

To hold plate(s) 10, each mounting plate 10 also includes a shelf 82 extending from the upper half of the back side 84 of rigid plate 14 (see FIG. 2). Shelf 82 may be used to secure the mounting plate 10 to an intravenous pole 12 or other external structure by way of clamping mechanism 85 as is well known in the art. As seen readily in FIG. 2, an upwardly facing hook 86 is molded into the back side of plate 14 near bottom edge 52 for suspending a solution reservoir (not shown), for example, from mounting plate 10. A slot 87 may be formed through plate 14 adjacent hook 86. A rectangular depression 88 may be formed in plate face 16 (FIG. 1) for attaching a label or other identification to the mounting plate 10.

In use (see FIG. 4), two mounting plates 10 are easily interconnected by sliding rib 24 of a first plate 10A into slot 38 of a second plate 10B laterally in the direction rib 24 extends from its rigid plate 14 as indicated by arrow A until detents 56 snap into rib notches 32 to thus rigidly, but releasably interlock mounting plates 10A, 10B together. Additional plates (e.g., 10C) may be locked to one of the first two (e.g., 10B) in similar fashion (see, e.g., FIG. 5) to thus provide a simulated single plate having as many support receptacles as needed. The device to be supported (e.g., transducer 20) may be mounted onto receptacles 18 before or after the plates are snapped together as desired. To separate the mounting plates, the proximal ends 58 of locking arms 46 are depressed towards the top and bottom edges 50, 52 while the units are simply slid apart in the opposite direction of their insertion. Thus, in accordance with the principles of the present invention, any number of mounting plates may be quickly and easily interconnected to form a system capable of supporting any desired number of devices. Additionally, the system may be easily, quickly and reliably separated into its individual mounting plates with minimal risk of exposure to edges and without the difficulty associated in a prior modular system.

Figure 7:
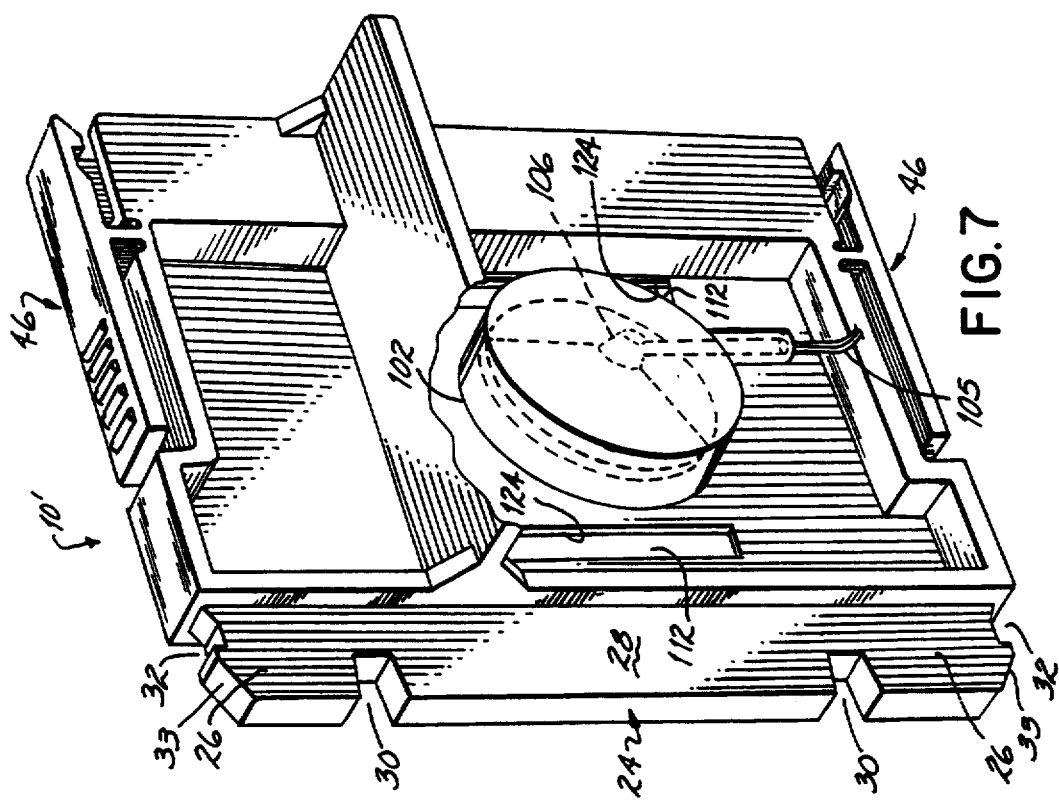
FIG. 7 is a rear perspective view of the mounting plate of FIG. 6.
Figure 6:
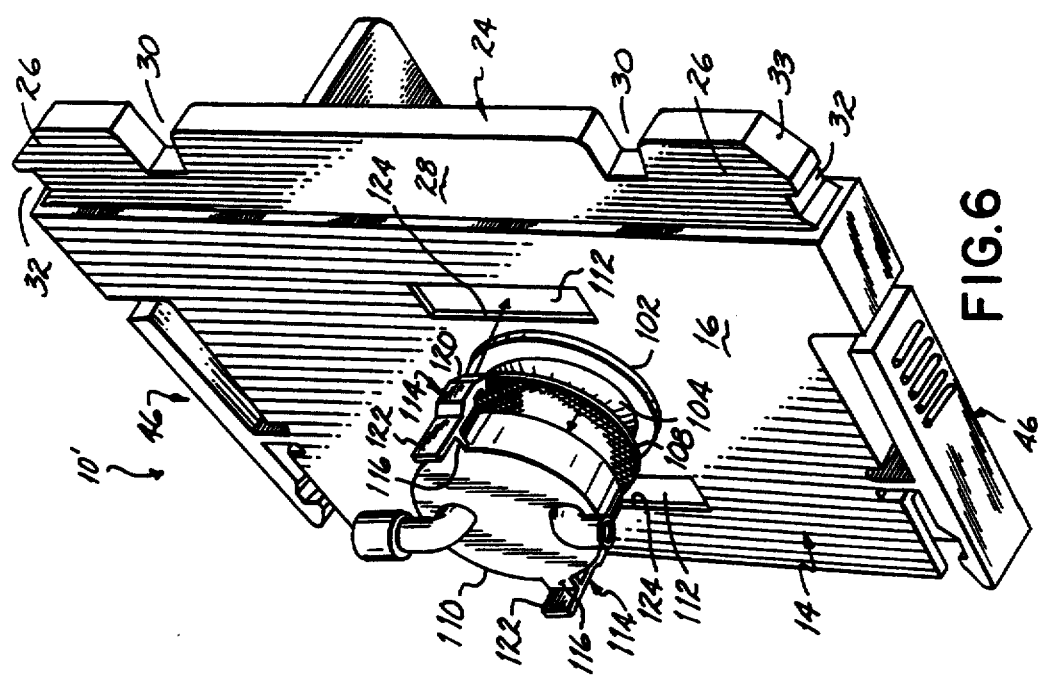
FIG. 6 is a front perspective view of another mounting plate in accordance with the principles of the present invention shown with the reusable portion of a medical transducer permanently attached thereto.

With reference to FIGS. 6 and 7, and in accordance with a further aspect of the invention, a modular system in accordance with the principles of the present invention may incorporate, in generally permanent fashion, a medical device therewith. By way of example, mounting plate 10' is similar to plate 10 but has the reusable portion of a medical device, such as a transducer 20, formed directly into rigid plate 14. To this end, and by way of example, rigid plate 14 has an aperture 102 formed therethrough with diaphragm 104 affixed to plate face 16 across aperture 102. A transducer sensor 106 is secured to rigid plate 14 behind aperture 102 and placed into communication with diaphragm 104, such as via a gel-filled recess, to fully perform the function of a reusable transducer portion. Wires 105 extend from sensor 106 to be coupled to a monitor (not shown). Sensor 106 may alternatively have electrical connectors extending therefrom for releasable attachment to a cable coupled to the monitor. The construction of sensor 106 and diaphragm 104 into a transducer may be as disclosed in U.S. Pat. No. 4,920,972, the disclosure of which is incorporated herein by reference.

To use sensor 106, reusable diaphragm 104 is to be placed into confronting engagement with the diaphragm 108 of a disposable fluid dome 110 (diaphragm 108 is secured to dome 110 but is shown separated therefrom in FIG. 6 for explanatory purposes). To this end, support structure is provided by a pair of slots 112 parallel to right and left side edges 22 and 34 of rigid plate 14 and extending through rigid plate 14 on opposing sides of aperture 102. Slots 112 are sized and positioned to receive locking arms 114 pivotally connected by pivot member 116 to fluid dome 110. Arms 114 have inwardly facing hooks 120 thereon. As locking arms 114 are inserted into slots 112, hooks 120 ride over inner edges 124 of slots 112, and when disposable dome diaphragm 108 is in confronting engagement with the reusable portion diaphragm 104, hooks 120 emerge through rigid plate 14 and locking arms 114 resume their undeformed shape thereby securely locking disposable portion 110 to mounting plate 10'.

To remove disposable portion 110, proximal ends 122 of locking arms 114 are inwardly depressed to pivot the distal ends 120 outwardly, thereby disengaging hooks 120 from the slot inner edges 124 whereby dome 110 may be slid free of the mounting plate 10'. Thus, in accordance with the present invention, a modular mounting plate incorporating the reusable portion of a medical device, such as a transducer, is provided that can easily and quickly receive the disposable portion thereof, and which can additionally be interlocked with any number of similar mounting plates to provide a system capable of holding any desired number of devices.

Figure 8:
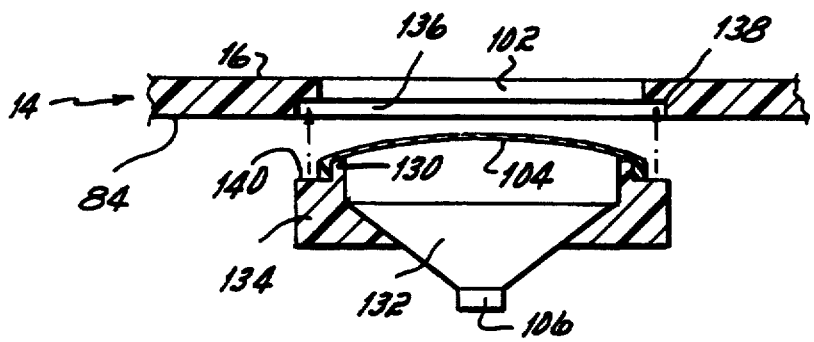
FIG. 8 is a cross-sectional side view of an alternative mounting arrangement of the reusable transducer portion of the plate FIG. 6.

As shown in FIG. 8, diaphragm 104 may alternatively extend across lip 130 of gel-filled cavity 132 contained within sensor housing 134. Recess 136 in the rigid plate back side 84, which is slightly larger in diameter than aperture 102, is sized to receive the sensor/diaphragm assembly such that shoulder 138 of recess 136 cooperates with housing 134 to hold diaphragm 104 to housing 134. Sensor housing 134 is fixedly secured to rigid plate 14 by ultrasonic welding or by applying adhesive to exposed surface 140 of the housing prior to pushing the housing against back side 84 of rigid plate 14. After securing the sensor/diaphragm assembly to the mounting plate, and after curing of the gel in cavity 132 as described in the aforementioned U.S. Pat. No. 4,920,972, diaphragm 104 bulbously protrudes through aperture 102 for communication with the diaphragm of a disposable fluid dome. Although FIG. 8 shows diaphragm 104 fixedly secured between sensor housing 134 and rigid plate 14, it will be appreciated by those skilled in the art that lip 130 may protrude through aperture 102 and forwardly thereof with diaphragm 104 fixedly secured across and solely to lip 130. Thus, sensor housing 134 and diaphragm 104 may protrude through aperture 102 and forwardly of face plate 16 such that diaphragm 104 is still accessible from the face of the plate in accordance with the principles of the present invention.

Figure 9:
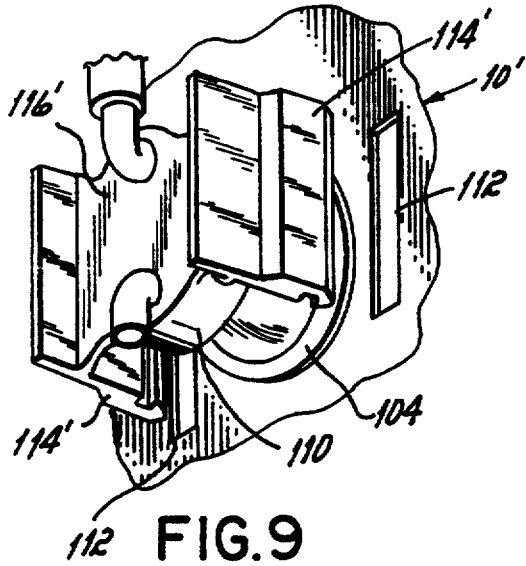
FIG. 9 is a perspective view of an alternative attachment structure to secure a fluid dome to the plate of FIG. 6.

It will be appreciated that other structures for releasably attaching a disposable medical device (e.g., a transducer dome) to the mounting plate may be used. For example, locking arms 114 could be extended as at 114' to substantially the length of slots 112 as shown in FIG. 9. For this purpose, pivot members 116 are replaced with connecting plate 116'.

Figure 10:
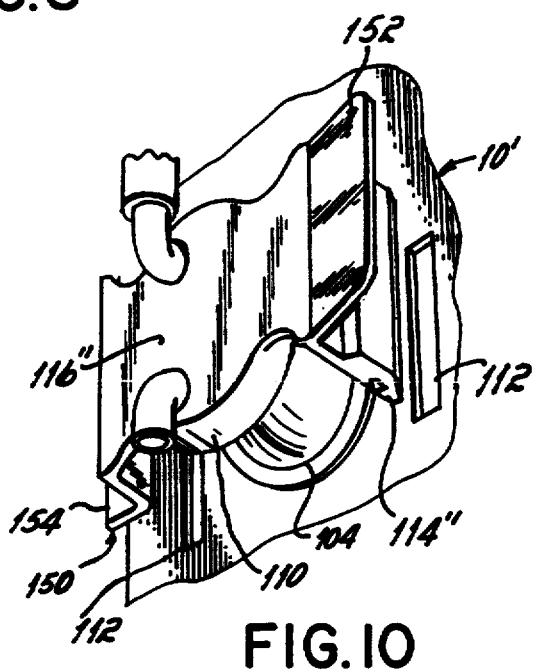
FIG. 10 is a perspective view of another alternative attachment structure to secure a fluid dome to the plate of FIG. 6.

Alternatively, a "ski-boot" foot and latching arm structure may be used as shown in FIG. 10. To this end, mounting plate 10' and reusable portion diaphragm 104 remain unchanged from that described above. However, the locking structure of disposable fluid dome 110 is replaced with an outwardly facing L-shaped foot 150 connected to one side of connecting plate 116" and extending forwardly therefrom, and an extended length latch member 114" on the other side of connecting plate 116", which is the same as that described above but with a lever arm 152 attached thereto for a purpose to be described. To secure fluid dome 110 to mounting plate 10', dome 110 is pivoted onto its side so that the free end 154 of foot 150 may be inserted into one of slots 112. Fluid dome 110 is then pivoted towards plate face 16 until latching member 114" locks into the other slot 112 thereby placing the respective diaphragms in confronting engagement. To remove the disposable fluid dome 110 of FIG. 10, lever arm 152 is lifted to disengage latch member 114" from mounting plate 10' and fluid dome 110 is pivoted, whereby foot 150 may be removed from slot 112 and fluid dome 110 lifted from mounting plate 10'. Although the locking structure of fluid dome 110 in FIGS. 9 and 10 is shown with connecting plate 116' and 116" extending from the top of fluid dome 110, it will be readily appreciated that the connecting plate 116' could be formed along the side or from the bottom of the fluid dome.

Figure 11:
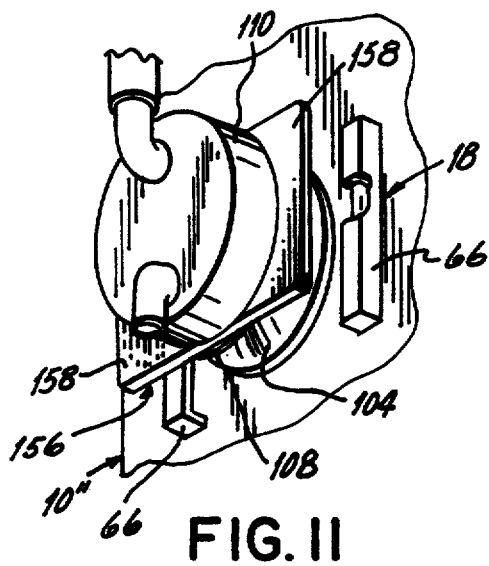
FIG. 11 is a perspective view of a modified plate to receive a fluid dome.

With reference to FIG. 11, receptacle 18 (i.e., channels 66) could be employed, as described in connection with FIG. 1, to secure fluid dome 110 to mounting plate 10". To this end, fluid dome 110 is constructed with bottom-mounted plate 156 that defines wings 158 for slidable engagement with channels 66 to hold the respective diaphragms 104, 108 into confronting engagement.

Figure 12:
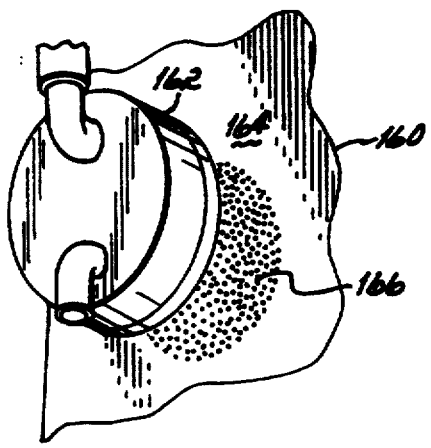
FIG. 12 is a perspective exploded view of a medical device permanently affixed to a modular plate in accordance with the principles of the present invention.

Referring to FIG. 12, a modular plate 160 made in accordance with a further aspect of the invention is shown having a medical device 162 permanently affixed to the face 164 of plate 160. Plate 160 may be the same as plates 10 and 10', except that face 164 may be solid without either slots or a receptacle. To this end, a medical device 162, such as a disposable pressure transducer, is fixedly adhered to solid front face 164 such as by way of adhesive 166 resulting in a generally permanent unitary structure. The plate with the medical device affixed thereto may be interconnected with other mounting plates (with or without permanently affixed medical devices). After use, the entire plate 160 is discarded. Although FIG. 12 shows medical device 162 secured to plate 160 by way of adhesive 166, it will be readily appreciated that other means of permanently including a medical device with the mounting plate may be used.

Also, the reusable portion of a two-part transducer could be formed on or adhered to the plate with the dome being removably affixed thereto by a threaded quarter-turn arrangement (not shown).

In manufacturing the mounting plates 10, 10', 10" and 160, any suitable plastic such as polycarbonate may be used in the molding process. Additionally, it would be desirable to mold the mounting plate as a single component, although a multi-component mounting plate would be within the principles of the invention. To create the single modular unit out of plastic, it will be appreciated that plate 14 should not be too thick. Thus, the top and side edges may actually be walls extending from face 16 as seen in FIG. 2.

By virtue of the foregoing, there is thus provided a modular interconnecting component mounting plate that may be easily and quickly connected with similar units to form a plate capable of supporting a number of devices, and which is easily separated into its constituent components for storage and reuse.

While the present invention has been illustrated by description of different embodiments which have been described in considerable detail, it is not the intention of the applicant to restrict or in any way limit the scope of the appended claims to such detail. Additional advantages will readily appear to those skilled in the art. For example, a mounting plate 10 including one or no locking arms 46 may be used and still fall within the principles of the present invention. With such a system, the mounting plates 10 are interconnected through a friction fit between the rib 24 and slot 38 of similar units. Additionally, a mounting plate 10 in which the rib middle segment 28 is removed will function within the principles herein. Also, where the medical device is permanently affixed, male-to-female mating structures other than as described herein may be employed. Thus, the invention in its broadest aspects is not limited to the specific details, representative apparatus and method, and illustrative example shown and described. Accordingly, departures may be made from the details without departing from the spirit or scope of applicant's general inventive concept.

What is claimed is:

1. A modular interconnecting support unit comprising:
    a rigid plate having a face, a surface of which defines a plane;
    component support structure associated with the plate face;
    a pair of sidewalls forming a slot extending from a first edge of the plate in a plane generally parallel to the plane defined by the plate surface; and
    a rib extending from a second, opposite edge of the plate in a plane generally parallel to the plane defined by the plate surface;
    whereby the rib of a first unit is slidably receivable into the slot of a second unit while the surfaces of the plate faces thereof are maintained in generally planar relationship.

2. The support unit of claim 1 further comprising:
    at least one rib stop within the slot and at least one recess formed in the rib whereby to prevent longitudinal sliding motion of a rib within a slot.

3. The support unit of claim 1 further comprising:
    releasable lock means associated with the slot and the rib to securely but releasably hold two such units together.

4. The support unit of claim 1 further comprising:
    at least one locking arm supported on the plate and adjacent a lateral end of the slot, the locking arm having structure adapted to grip a lateral end of a rib received in the slot.

5. The support unit of claim 4, the lateral end of the slot being open for a lateral end of the rib to protrude therefrom, the lateral end of the rib having a recess to receive a portion of the locking arm therein.

6. The support unit of claim 1 wherein the plate includes an intermediate edge extending between the first and second edges, the unit further comprising at least one locking arm pivotally mounted to the intermediate edge and having a distal portion adjacent the slot and a proximal portion spaced away from the slot and towards the rib.

7. The support unit of claim 6, the intermediate edge including a recessed portion in which the locking arm is situated whereby to reduce exposure to edges.

8. The support unit of claim 1 further comprising a medical device permanently affixed to the plate.

9. The support unit of claim 8, the medical device being a reusable portion of a pressure transducer with a sensor and a diaphragm in communication with one another, the medical device being affixed to the plate with the diaphragm accessible from the face of the plate.

10. The support unit of claim 9, the plate face including an aperture, the reusable pressure transducer diaphragm being affixed across the aperture.

11. The component support unit of claim 9 wherein the component support structure comprises a pair of opposed L-shaped walls to either side of the medical device and being substantially parallel to the first and second edges and extending forwardly from the face with ledges at the bottom end thereby forming a pair of confronting channels.

12. The component support unit of claim 11 in combination with a disposable portion of the reusable pressure transducer and having a disposable diaphragm thereon, the disposable portion including a pair of wings extending from opposing sides for sliding engagement with the confronting channels for placing said disposable portion diaphragm in pressure communication with the reusable pressure transducer diaphragm.

13. The component support unit of claim 9 wherein the component support structure comprises a pair of slots to either side of the medical device.

14. The component support unit of claim 13 in combination with the disposable portion of a medical device having a diaphragm thereon and including a pair of locking arms pivotally mounted on opposing sides adapted to be received by the pair of slots for releasably locking said disposable portion to the plate thereby placing said disposable portion diaphragm in pressure communication with the diaphragm on the plate.

15. The component support unit of claim 13 in combination with the disposable portion of a medical device having a diaphragm thereon and including an outwardly facing L-shaped foot extending forwardly from one side thereof adapted to be pivotally received by one of the slots and a flexible latching arm extending forwardly from the opposing side adapted to be received by the other slot for releasably locking said disposable portion to the plate thereby placing said disposable portion diaphragm in pressure communication with the diaphragm on the plate.

16. The component support unit of claim 1 wherein the component support structure comprises a pair of opposed L-shaped walls substantially parallel to the first and second edges and extending forwardly from the face with ledges at the bottom end thereby forming a pair of confronting channels.

17. A modular interconnecting component support unit comprising:

a rigid plate having a generally planar face and component support structure associated with the plate face and structure for mounting the support unit to an external support;

a rib extending from a first edge of the plate in a direction generally parallel to the plate face and having a notch on each lateral end thereof;

a pair of walls forming a slot extending from a second, opposite edge of the plate in a direction generally parallel to the plate face;

a pair of pivotable locking arms mounted on third and fourth spaced apart edges of the plate which are intermediate the first and second edges, a distal end of each arm extending over the slot and having a finger thereon adapted to fit into the notch of a rib received in the slot, a proximal end of each arm being movable toward the plate to lift the finger from the notch;

whereby when the rib of one such unit is inserted into the slot of another such unit in a direction generally parallel to the plate face, the locking arm fingers fit into the rib notches to releasably and rigidly interconnect the units.

18. The support unit of claim 17 further comprising:

at least one rib stop within the slot and at least one recess formed in the rib whereby to prevent longitudinal sliding motion of a rib within a slot.

19. The support unit of claim 17, the third and fourth edges each including a recessed portion into which the respective locking arm is situated whereby to reduce exposure to edges.

20. The support unit of claim 17 further comprising a medical device permanently affixed to the plate.

21. The support unit of claim 20, the medical device being a reusable portion of a pressure transducer with a sensor and a diaphragm in communication with one another, the medical device being affixed to the plate with the diaphragm being accessible at the face of the plate.

22. The support unit of claim 21, the plate face including an aperture, the reusable pressure transducer diaphragm being affixed across the aperture.

23. The component support unit of claim 21 wherein the component support structure comprises a pair of opposed L-shaped walls to either side of the medical device and being substantially parallel to the first and second edges and extending forwardly from the face with ledges at the bottom end thereby forming a pair of confronting channels.

24. The component support unit of claim 23 in combination with a disposable portion of the reusable pressure transducer and having a disposable diaphragm thereon, the disposable portion including a pair of wings extending from opposing sides for sliding engagement with the confronting channels for placing said disposable portion diaphragm in pressure communication with the reusable pressure transducer diaphragm.

25. The component support unit of claim 21 wherein the component support structure comprises a pair of slots to either side of the medical device.

26. The component support unit of claim 25 in combination with the disposable portion of a medical device having a diaphragm thereon and including a pair of slots locking arms pivotally mounted on opposing sides adapted to be received by the pair of slots for releasably locking said disposable portion to the plate thereby placing said disposable portion diaphragm in pressure communication with the diaphragm on the plate.

27. The component support of claim 25 in combination with the disposable portion of a medical device having a diaphragm thereon and including an outwardly facing L-shaped foot extending forwardly from one side thereof adapted to be pivotally received by one of the slots and a flexible latching arm extending forwardly from the opposing side adapted to be received by the other slot for releasably locking said disposable portion to the plate thereby placing said disposable portion diaphragm in pressure communication with the diaphragm on the plate.

28. A modular interconnecting medical device support unit comprising:
   a rigid plate;
   a medical device permanently affixed to the plate;
   a first connector portion associated with a first edge of the plate; and
   a second connector portion associated with a second, opposite edge of the plate, the second connector portion being adapted to couple to a respective first connector portion of another such unit.

29. The support unit of claim 28 wherein the plate has a face and an aperture therethrough, the medical device including a diaphragm accessible from the plate face and a sensor held in pressure communication with the diaphragm, the plate further having support structure associated therewith for releasably holding a removable pressure communicating device against the diaphragm.

30. The support unit of claim 29, the diaphragm being affixed across the aperture.

31. The support unit of claim 29, the device further including a sensor housing with the diaphragm mounted thereto, the plate including a recess about the aperture, the recess and housing cooperating to wedgingly hold a diaphragm to the sensor housing.

32. The support unit of claim 29 wherein the support structure includes a pair of opposed L-shaped walls to either side of the diaphragm and being substantially parallel to the first and second edges and extending forwardly from the face with ledges at the bottom end thereby forming a pair of confronting channels.

33. The support unit of claim 32 in combination with a removable pressure communication device having a disposable diaphragm thereon and a pair of wings extending from opposing sides for sliding engagement with the confronting channels for placing said disposable diaphragm in pressure communication with the medical device diaphragm.

34. The transducer support unit of claim 29 wherein the support mechanism includes a pair of slots to either side of the reusable diaphragm.

35. The transducer support unit of claim 34 in combination with a removable pressure communication device having a disposable diaphragm thereon and a pair of locking arms pivotally mounted on opposing sides adapted to be received by the slots for releasably locking said removable pressure communicating device to the plate thereby placing said disposable diaphragm in pressure communication with the medical device diaphragm.

36. The transducer support unit of claim 34 in combination with a removable pressure communication device having a disposable diaphragm thereon and an outwardly facing L-shaped foot extending forwardly from one side thereof adapted to be pivotally received by one of the slots and a flexible latching arm extending forwardly from the opposing side adapted to be received by the other slot for releasably locking said removable pressure communicating device to the plate thereby placing said disposable diaphragm in pressure communication with the medical device diaphragm.

37. The support unit of claim 28 wherein the rigid plate has a face, the medical device being adhesively affixed to the plate face.

38. The support unit of claim 28 wherein the medical device is a disposable medical pressure transducer.

39. The support unit of claim 28 further comprising cooperating locking structure associated with the first connector portion and second connector portion to securely lock two such units together with the first connector portion of one unit coupled to the second connector portion of another unit.

40. The support unit of claim 28 wherein the first connector portion is a male web and the second connector portion is a female receptacle sized to receive therein a male web of another such unit.

41. A modular interconnecting component support unit comprising:
   a rigid plate having a generally planar face;
   component support structure associated with plate face;
   a male web associated with a first edge of said plate;
   a female receptacle associated with a second, opposite edge of the plate and sized to receive therein the male web of another unit; and
   locking structure associated with each of a third and fourth edge intermediate the first and second edges and positioned to grip the male web of another such unit received in the female receptacle.

42. A modular interconnecting support unit comprising:
   a rigid plate having a face;
   a male web associated with a first edge of the plate; and
   a female receptacle associated with a second, opposite edge of the plate and sized to receive therein the male web of another unit whereby the male web of a first unit is receivable into the female receptacle of a second unit to interconnect the units; and
   a portion of a medical pressure transducer having a sensor and a diaphragm in communication with one another, the transducer portion being permanently affixed to the plate with the diaphragm accessible from the face of the plate.

* * * * *

UNITED STATES PATENT AND TRADEMARK OFFICE
CERTIFICATE OF CORRECTION

PATENT NO. : 5,417,395
DATED : May 23, 1995
INVENTOR(S) : James Fowler et al

It is certified that error appears in the above-indentified patent and that said Letters Patent is hereby corrected as shown below:

Column 10, lines 62-63, "pair of slots locking arms"

should read --pair of locking arms--.

Signed and Sealed this

Twentieth Day of February, 1996

Attest:

BRUCE LEHMAN

Attesting Officer

Commissioner of Patents and Trademarks